(12) United States Patent
Oishi

(10) Patent No.: US 9,170,247 B2
(45) Date of Patent: Oct. 27, 2015

(54) CONCENTRATION MEASURING DEVICE

(71) Applicant: Daiki Rika Kogyo Co., Ltd., Kounosu-shi, Saitama (JP)

(72) Inventor: Masayuki Oishi, Saitama (JP)

(73) Assignee: DAIKI RIKA KOGYO CO., LTD., Kounoso-Shi, Saitama (JP)

( * ) Notice: Subject to any disclaimer, the term of this patent is extended or adjusted under 35 U.S.C. 154(b) by 25 days.

(21) Appl. No.: 14/086,508

(22) Filed: Nov. 21, 2013

(65) Prior Publication Data

US 2014/0170738 A1    Jun. 19, 2014

(30) Foreign Application Priority Data

Dec. 18, 2012  (JP) .................................. 2012-275611
Oct. 17, 2013  (JP) .................................. 2013-216317

(51) Int. Cl.
| G01N 15/06 | (2006.01) |
| G01N 33/00 | (2006.01) |
| G01N 33/48 | (2006.01) |
| G01N 33/24 | (2006.01) |

(52) U.S. Cl.
CPC .......... *G01N 33/0013* (2013.01); *G01N 33/241* (2013.01)

(58) Field of Classification Search
USPC .............. 422/50, 68.1, 502, 503, 504; 436/43
See application file for complete search history.

(56) References Cited

U.S. PATENT DOCUMENTS 5,279,970 A    1/1994    Patashnick et al.

FOREIGN PATENT DOCUMENTS

| DE | 28 21 190 B1 | 8/1979 |
| JP | 2001-41916 A | 2/2001 |
| JP | 2011-232333 | 11/2011 |
| WO | WO 2010/025600 A1 | 3/2010 |

OTHER PUBLICATIONS

European Search Report issued in Appln. No. 13193792.2 dated Apr. 22, 2015 (5 pages).

*Primary Examiner* — Brian J Sines
(74) *Attorney, Agent, or Firm* — Flynn, Thiel, Boutell & Tanis, P.C.

(57) ABSTRACT

A concentration measuring device with which the concentration measurement of a test substance can be facilitated as compared to a conventional technique is provided. The concentration measuring device includes: first to third pipes together forming a circulation path through which a gas can circulate; a pump for flowing the gas in a circulating direction in the circulation path; a sample disposed in the circulation path; and a concentration measuring mechanism for measuring a concentration of a target substance from the sample in the circulation path. The concentration measuring mechanism includes, for example, a sample heater, a catalyst, a catalyst heater, a detection chamber, a concentration sensor, and a control unit.

15 Claims, 16 Drawing Sheets

| PROCESS TYPE | 81 | 82 | 83 | 84 |
|---|---|---|---|---|
| PIPES 21-23 | A | A | B | A |
| HEATER 63 | OFF | ON | ON | OFF |

Fig. 14

| PROCESS TYPE | 81 | 82 | 83 | 84 | 83 | 84 |
|---|---|---|---|---|---|---|
| PIPES 121, 22, 23 | A | A | B | A | B | A |
| SAMPLE HEATER 163S | OFF | OFF | ON | OFF | ON | OFF |
| CATALYST HEATER 163C | OFF | ON | ON | ON | ON | OFF |

CONCENTRATION MEASURING DEVICE

BACKGROUND OF THE INVENTION

1. Field of the Invention

The present invention relates to a concentration measuring device.

2. Description of the Related Art

There is known a concentration measuring device that measures a concentration of a test substance in a gas. For example, a device disclosed in Patent Literature 1 measures an amount of a petroleum-based hydrocarbon contained in soil by detecting the concentration of carbon dioxide generated by the combustion of the hydrocarbon. The concentration measuring device includes: a heater for heating a mixed gas containing oxygen and nitrogen; a soil case for holding soil; a catalyst case for holding a catalyst; and a concentration sensor for measuring a concentration of carbon dioxide.

When the soil is exposed to the heated mixed gas in the device disclosed in Patent Literature 1, the hydrocarbon component contained in the soil is vaporized. Furthermore, when the vaporized hydrocarbon component comes into contact with the catalyst, predetermined amounts of water and carbon dioxide are generated due to a reaction of the hydrocarbon component with the oxygen in the mixed gas. Since the reaction using the catalyst is known, the concentration of the hydrocarbon component contained in the initial soil can be calculated from the concentration of carbon dioxide detected by the concentration sensor. Finally, the gas having passed through a concentration detection chamber housing the concentration sensor is discharged directly into outside air.

Patent Literature 1: Japanese Patent Application Laid-open No 2011-232333 is introduced as the Prior Art Document.

In a case where the device described in Patent Literature 1 is used for a gas having a test substance in a low concentration, however, the concentration of carbon dioxide generated by a reaction with a catalyst may fall below a concentration range detectable by the concentration sensor. If a volume flow of the gas is increased in the vicinity of the concentration sensor, for example, the concentration detected by the concentration sensor is decreased. Thus, it is impossible to measure the concentration of carbon dioxide if it falls below the concentration range measurable by the concentration sensor. Therefore, in the device of Patent Literature 1, a level of accuracy required in gas flow control becomes high. Such a problem can be solved tentatively by employing a highly-sensitive concentration sensor. However, such a highly-sensitive concentration sensor has disadvantages such that it is expensive and handling thereof such as calibration is not easy.

SUMMARY OF THE INVENTION

The present invention has been made in view of the aforementioned problems. It is an object of the invention to provide a concentration measuring device with which the concentration measurement of a test substance can be facilitated as compared to a conventional technique.

The concentration measuring device of the present invention includes: a circulation path forming member that forms a circulation path through which a gas can circulate; a circulation device for flowing the gas in a predetermined circulating direction in the circulation path; and a concentration measuring mechanism for measuring a concentration of a target substance from a sample in the circulation path. The concentration measuring mechanism preferably includes: a sample heater for heating the sample; a catalyst located in the circulation path downstream of the sample in the circulation direction; a catalyst heater for heating the catalyst; a test substance detecting part provided in the circulation path downstream of the catalyst in the circulating direction, for detecting a test substance generated by a reaction between the catalyst and the target substance; a concentration sensor for detecting a concentration of the test substance in the test substance detecting part; and an output part for outputting the concentration of the test substance detected by the concentration sensor to a calculation part that calculates a concentration of the target substance from the concentration of the test substance. The circulation path preferably includes a return path for allowing the gas exiting from the test substance detecting part to be returned to the sample. The concentration sensor preferably detects a concentration of the test substance for the gas having passed through the return path.

Preferably, the concentration measuring device further includes a sample container for holding the sample therein and a catalyst container for holding the catalyst therein, and a relative position between the catalyst container or the catalyst heater and the sample container can be switched between a first state in which they are separated from each other and a second state in which they are closer to each other as compared to the first state. Preferably, the sample container is movable, whereas the catalyst container is fixed.

Preferably, the concentration measuring device further includes a heater controlling part for controlling the sample heater and the catalyst heater, and the heater controlling part controls the sample heater in such a manner that heating of the sample is performed in the second state and heating of the sample is stopped in the first state, and controls the catalyst heater in such a manner that heating of the catalyst is performed in each of the first state and the second state.

Preferably, the concentration measuring device further includes a controlling part for controlling the sample heater and the catalyst heater, and the controlling part controls to perform heating of the sample and the catalyst in a step of measuring a concentration of the target substance and controls to perform heating of the catalyst and stop heating of the sample before or after the step of measuring the concentration of the target substance.

Preferably, the catalyst heater and the sample heater are integrally formed.

Preferably, the concentration measuring device further includes a switching mechanism capable of switching the circulation path forming member between an air intake and exhaust state in which an outside air is introduced toward the sample and the gas exiting from the test substance detecting part is discharged to an outside and a circulation state in which the gas exiting from the test substance detecting part is returned to the sample.

Preferably, the concentration measuring device further includes a cooling device for cooling the catalyst or the sample, and the cooling device includes a switching mechanism capable of switching the circulation path forming member between an air intake and exhaust state in which an outside air is introduced toward the sample and the gas exiting from the test substance detecting part is discharged to an outside and a circulation state in which the gas exiting from the test substance detecting part is returned to the sample.

Preferably, the switching mechanism includes a first switching valve provided in the circulation path between the sample and the test substance detecting part, a second switching valve provided in the circulation path between the first switching valve and the test substance detecting part, and a switching valve controller for controlling the first and second switching valves; each of the first and second switching valves can preferably change a path between an open state in which the circulation path is opened to the outside and a closed state in which the circulation path is closed off from the outside; and the switching valve controller sets the first and second switching valves to the open state so that the circulation path forming member is set in the air intake and exhaust state and sets the first and second switching valves to the closed state so that the circulation path forming member is set in the circulation state.

When a process of causing the concentration sensor to detect a concentration of the test substance in the test substance detecting part while the first and second switching valves are both in the closed state and the sample heater and the catalyst heater are turned ON is defined as a main measurement process, it is preferable that the switching valve controller maintain the first and second switching valves in the closed state until passage of a predetermined amount of time after start of the main measurement process and change both of the first and second switching valves to the open state once the predetermined amount of time has elapsed.

Preferably, the concentration measuring device further includes a flow path volume changing mechanism capable of changing a volume of a flow path formed by the circulation path forming member.

Preferably, the concentration measuring device further includes an upstream-side concentration sensor disposed upstream of the sample in the circulating direction, for detecting a concentration of the test substance.

According to the concentration measuring device of the present invention, the concentration measurement of a test substance can be facilitated as compared to the conventional technique.

BRIEF DESCRIPTION OF THE DRAWINGS

FIG. 14 is a table showing state transition of each pipe and each heater in each of the processes;

DETAILED DESCRIPTION OF THE PREFERRED EMBODIMENTS

Embodiments of the present invention will now be described below with reference to the accompanying drawings.

Figure 1:
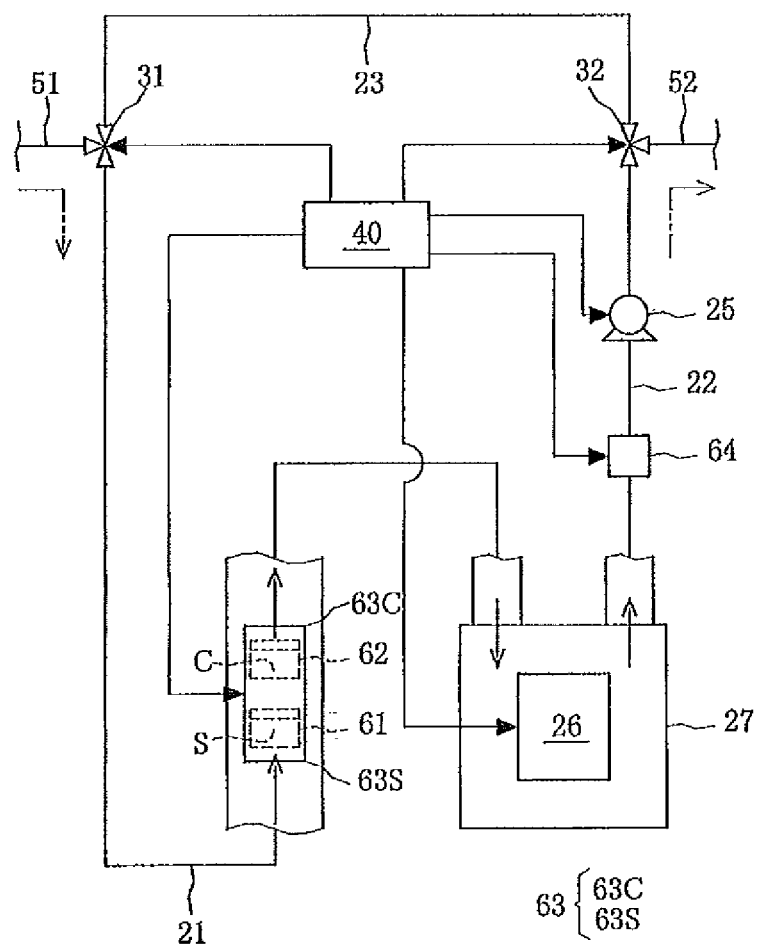
FIG. 1 is an explanatory diagram showing an outline of a first concentration measuring device with pipes set in an air intake and exhaust state.

As shown in FIG. 1, a concentration measuring device 10 is used for measuring a concentration of a target substance contained in a sample S. The concentration measuring device 10 includes: first to third pipes 21 to 23 together forming a circulation path; a pump 25; a concentration sensor 26; a detection chamber 27 housing the concentration sensor 26 therein; first and second three-way valves 31 and 32 making up a switching mechanism; and a control unit 40 for controlling these components.

The first to third pipes 21 to 23 are each a member for forming a circulation path. Besides a material having a thermal conductivity, an insulator material may be used as a material for forming the first to third pipes 21 to 23. The first pipe 21 connects between the first three-way valve 31 and an inlet of the detection chamber 27. The second pipe 22 connects between an outlet of the detection chamber 27 and the second three-way valve 32. The third pipe 23 connects between the first and second three-way valves 31 and 32. The circulation path formed by the first to third pipes 21 to 23 has an airtight property and has a shape through which a gas can circulate.

The first three-way valve 31 is connected to an intake pipe 51 whose opening is in communication with the outside. The second three-way valve 32 is connected to an exhaust pipe 52 whose opening is in communication with the outside. The respective first and second three-way valves 31 and 32 can change the state of the path between an open state (see FIG. 1) in which the first and second pipes 21 and 22 are opened to the outside and a closed state (see FIG. 2) in which the circulation path by the first to third pipes 21 to 23 is closed off from the outside.

The open state of the first three-way valve 31 may refer to either a state in which only the first pipe 21 and the intake pipe 51 are in communication with each other or a state in which the first pipe 21, the third pipe 23, and the intake pipe 51 are in communication with one another. Similarly, the open state of the second three-way valve 32 may refer to either a state in which only the second pipe 22 and the exhaust pipe 52 are in communication with each other or a state in which the second pipe 22, the third pipe 23, and the exhaust pipe 52 are in communication with one another.

The control unit 40 switches between a circulation state (see FIG. 2) in which both of the first three-way valve 31 and the second three-way valve 32 are set to the closed state and an air intake and exhaust state (see FIG. 1) in which both of the first three-way valve 31 and the second three-way valve 32 are set to the open state.

The pump 25 is a circulation device for flowing a gas in a predetermined circulating direction D1 (see FIG. 2) in the circulation path and provided in the second pipe 22. Note that the pump 25 may be provided in the first pipe 21 instead. Above all, the pump 25 may be provided at a portion of the first pipe 21 upstream of the sample container 61. Providing the pump 25 at such a position makes it easier for the heat of the gas in the circulation path to be transferred to the sample container 61.

The detection chamber 27 is provided in a portion of the first pipe 21 downstream of a catalyst container 62 in the circulating direction D1. The concentration sensor 26 housed in the detection chamber 27 detects a concentration of a test substance contained in a gas in the detection chamber 27. According to the concentration measuring device 10 shown in the figures, the concentration sensor 26 is a carbon dioxide concentration sensor capable of detecting a carbon dioxide concentration.

The concentration measuring device 10 further includes; a sample container 61 for holding the sample S therein; the catalyst container 62 for holding a catalyst C therein; a heater 63 for heating the catalyst C; and a flow sensor 64. The sample container 61, the catalyst container 62, and the heater 63 are provided in the first pipe 21. Furthermore, the sample container 61, the catalyst container 62, and the heater 63 are preferably provided in a portion of the first pipe 21 extending from the lower side to the upper side in a direction from the upstream side toward the downstream side.

The heater 63 includes a sample heater 63S for heating the sample S held in the sample container 61 and a catalyst heater 63C for heating the catalyst C held in the catalyst container 62. The sample heater 63S and the catalyst heater 63C are arranged side by side in the circulating direction D1 within the first pipe 21. The sample heater 63S is provided around the sample container 61 and the catalyst heater 63C is provided around the catalyst container 62. Preferably, the sample heater 63S and the catalyst heater 63C each are formed in a tubular shape and the sample container 61 and the catalyst container 62 are housed in the internal spaces thereof, respectively. Note that the sample heater 63S and the catalyst heater 63C may be formed integrally. The sample heater 63S and the catalyst heater 63C are individually controlled by the control unit 40.

Figure 3A:
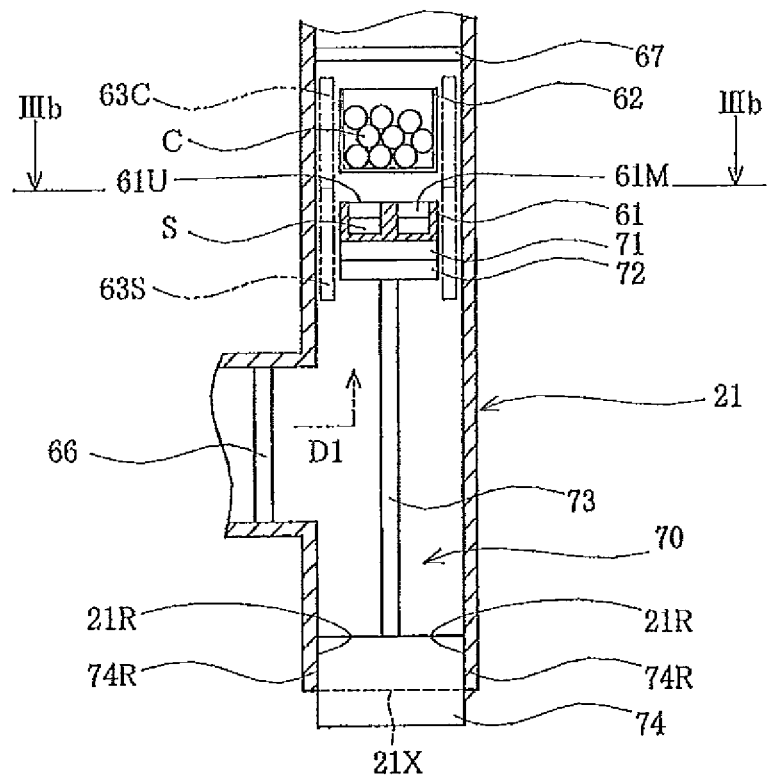
FIG. 3A is a cross-sectional view taken along line IIIa-IIIa of FIG. 3B showing an outline of a sample container and a first pipe.
Figure 3B:
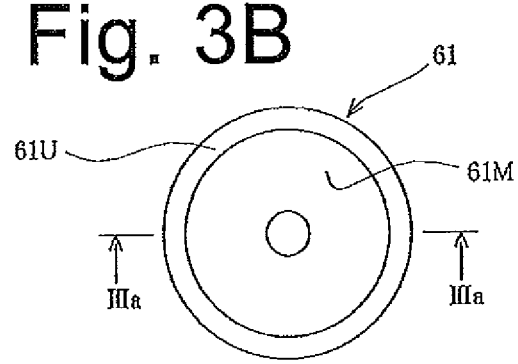
FIG. 3B is a plan view of the sample container as viewed in a direction of IIIb in FIG. 3A.

As shown in FIG. 3, the sample container 61 has a cylindrical shape and has a groove 61M on an upper surface 61U. The groove 61M is a space for holding the sample S. Although a shape of the groove 61M is not limited to any particular shape, a linear shape or the like may be employed besides a ring shape as shown in the figure. Alternatively, one or more depressed portions may be provided on the upper surface 61U as a substitute for the groove 61M. The sample container 61 is formed from a high thermal conductive material (for example, a metal, stainless steel, or the like).

A sample container holder 70 is further provided below the sample container 61 (the upstream side in the first pipe 21). The sample container holder 70 includes: a heat insulating plate 71 with an upper surface serving as a surface on which the sample container 61 is placed; a support plate 72 for supporting a lower surface of the heat insulating plate 71; a support rod 73 extending from a lower surface of the support plate 72; and a cylindrical knob 74 provided at a lower end of the support rod 73.

A predetermined gap is formed between the sample container 61 and the sample heater 63S. This gap serves as a flow path for a gas flowing through the first pipe 21. In a similar manner, a predetermined gap, such as one serving as a flow path for a gas, is formed also between the heat insulating plate 71 and the sample heater 63S and between the support plate 72 and the sample heater 63S.

The heat insulating plate 71 is formed from a low thermal conductive material (for example, ceramics or the like). The heat insulating plate 71 can prevent heat from the sample heater 63S from transferring to the support plate 72. Moreover, the heat insulating plate 71 supports the sample container 61 so as to cover the entire bottom surface of the sample container 61. Furthermore, the ring-shaped groove 61M formed on the upper surface 610 of the cylindrical sample container 61 contains the sample. Therefore, a gas flowed from the lower side (the upstream side in the first pipe 21) passes through the portion between the sample container 61 and the sample heater 638 while being in direct contact with the sample container 61 without being in direct contact with the sample S. As a result, it is possible to heat the sample S and to prevent the generation of dust caused by the gas being in contact with the sample S and the circulation of such dust.

A finger screw 74R is formed on a peripheral surface of the knob 74. An opening 21X used for bringing the sample container 61 or the like into or out from the first pipe 21 is formed midway in the first pipe 21. A pipe thread 21R to be screwed with the finger screw 74R formed on the knob 74 is provided on an inner wall surface of the first pipe 21 forming the opening 21X.

The sample container 61 is inserted into the first pipe 21 through the opening 21X using the sample container holder 70. Thereafter, the finger screw 74R is screwed with the pipe thread 21R so as to fix the sample container 61 inside the first pipe 21 with being housed in the sample heater 63S. Conversely, by releasing the screwing between the finger screw 74R and the pipe thread 21R, the sample container 61 can be movable between a state closer to the catalyst container 62 and the catalyst heater 63C and a state away from the catalyst container 62 and the catalyst heater 63C. In other words, by releasing the screwing between the finger screw 74R and the pipe thread 21R, the sample container 61 can be movable in the first pipe 21 in the vertical direction thereof.

The catalyst container 62 is provided in a portion of the first pipe 21 downstream of the sample container 61 in the circulating direction D1. The catalyst container 62 is formed from mesh. The catalyst container 62 is fixed in the first pipe 21 by means of a fixture not shown in the figure. Therefore, the catalyst C held in the catalyst container 62 can come into contact with a gas around the catalyst container 62. Also, the catalyst container 62 is preferably provided above the sample container 61. This makes it easier for a substance vaporized from the sample S to be in direct contact with the catalyst C. Since the mesh used for the catalyst container 62 can prevent the circulation of dust caused by the sample 8, only the component vaporized from the sample S can be supplied to the catalyst C.

The sample S is a sample containing a target substance, for example. Examples of such a sample S may include a matter containing a target substance (for example, a petroleum-based hydrocarbon). Examples of such a matter may include soil and the like. Such a matter is in the form of a solid (including a lump form and a powder form), a liquid, or the like and any form may be employed.

The catalyst C is used when the target substance cannot be directly detected by the concentration sensor 26. According to the concentration measuring device 10 shown in the figures, the target substance is a petroleum-based hydrocarbon (for example, light oil, kerosene, or heavy oil) or the like. Thus, a substance capable of generating carbon dioxide by the combustion of the petroleum-based hydrocarbon is used as the catalyst C.

The flow sensor 64 is provided in the second pipe 22 and detects a volume flow of a gas flowing through the second pipe 22. Note that the flow sensor 64 may be provided in the first pipe 21.

Preferably, upstream mesh 66 is provided in a portion upstream of the sample container 61 and downstream mesh 67 is provided in a portion downstream of the catalyst container 62 inside the first pipe 21. The upstream mesh 66 and the downstream, mesh 67 can reliably prevent the circulation of dust caused by the sample S.

Figure 4:
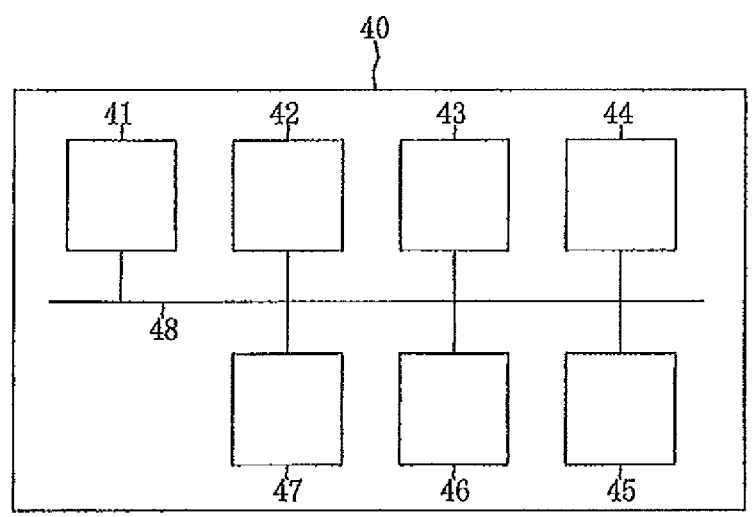
FIG. 4 is a block diagram showing an outline of a control unit.

As shown in FIG. 4, the control unit 40 includes: a CPU 41; a RAM 42; a ROM 43; a storage medium 44; an input device 45; an output device 46; an input-output interface 47; and a bus 48.

The CPU 41 is what is called a central processing unit and runs various programs to realize various functions of the control unit 40. The RAM 42 is used as a work area for the CPU 41. The ROM 43 stores a basic operating system (OS) to be run on the CPU 41. The storage medium 44 is composed of a hard disk drive with a built-in magnetic disk, a non-volatile semiconductor flash memory device, and the like. The storage medium 44 stores various programs to be run on the CPU 41 (a measured data calculation program, a measured data storing program, and the like).

The input device 45 may be an input key, an operating switch, or the like. The input device 45 is used for inputting various information. The output device 46 may be a display or a printer. The output device 46 displays or prints out various operational states. The input-output interface 47 is used for establishing a communication path with external devices such as the pump 25, the first and second three-way valves 31 and 32, the heater 63, and the sensors. The bus 48 integrally connects the CPU 41, the ROM 93, the RAM 42, the storage medium 44, the input device 45, the output device 46, the input-output interface 47, and the like so as to function as a communication line.

The control unit 40 controls the pump 25 on the basis of a sensing signal from the flow sensor 64. This makes it possible to keep the flow rate of the gas flowing through the second pipe 22 constant. In a case where no feedback control for a gas flow rate is needed depending on a type of the concentration sensor or the like, control for the flow rate of the gas flowing through the second pipe 22, which is performed on the basis of the sensing signal from the flow sensor 64, may be omitted.

A concentration measuring method performed by the concentration measuring device 10 will now be described below.

Figures 5A, 5B:
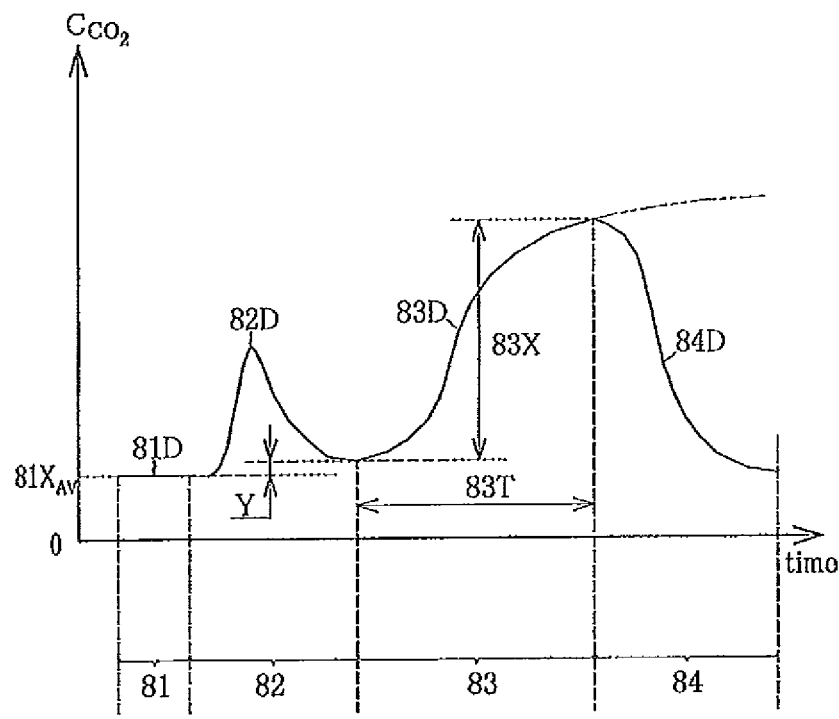
FIG. 5A is a graph showing a transition of detected values from a concentration sensor in each of processes when the first concentration measuring device is used, with the vertical axis thereof indicating a concentration of carbon dioxide detected by the concentration sensor and the horizontal axis thereof indicating time.
FIG. 5B is a table showing state transition of each pipe and a heater in each of the processes.

As shown in FIGS. 5A and 5B, the concentration measuring method performed by the concentration measuring device 10 includes: a background measurement process 81; a discharging process 82; a main measurement process 83; and a cooling process 84. The background measurement process 81 is performed prior to the main measurement process 83. In the background measurement process 81, a concentration of a test substance in outside air brought into the detection chamber 27 (see FIG. 1) is measured. The discharging process 82 is effective in a case where the catalyst C used has an ability to adsorb the test substance thereon in a state before being heated (low-temperature range) and has a property such that the ability to adsorb the test substance thereon is lost or decreased in a state after being heated (high-temperature range). In other words, in the discharging process 82, the catalyst C with the test substance adsorbed thereon in the low-temperature range is heated so as to discharge carbon dioxide adsorbed onto the catalyst C into the outside air. In the main measurement process 83, the concentration of the test substance is measured while both of the sample S and the catalyst. C are being heated. In the cooling process 84, the sample S is cooled by an operation of the first and second three-way valves 31 and 32 in order to take out the sample S. Note that the catalyst C may be cooled in order to take out the catalyst C along with the cooling of the sample S.

The discharging process 82 is performed because the catalyst C used in the above-described embodiment has an ability to adsorb the test substance thereon in a state before being heated (low-temperature range) and has a property such that the ability to adsorb the test substance thereon is lost or decreased in a state after being heated (high-temperature range). However, the present invention is not limited thereto. In other words, in a case where the catalyst C has no ability to adsorb the test substance thereon in the state before being heated (low-temperature range), or in a case where the catalyst C has an ability to adsorb the test substance thereon in the state before being heated (low-temperature range) but the magnitude of the adsorption ability is independent of the temperature thereof, the discharging process 82 may be omitted.

Details of the respective processes will now be described below.

<Background Measurement Process>

First, the control unit 40 controls the first and second three-way valves 31 and 32 to set the first to third pipes 21 to 23 to the air intake and exhaust state (see FIG. 1, denoted as "A" in FIG. 5B). As a result; outside air is directly discharged from the exhaust pipe 52 after passing through the intake pipe 51, the first pipe 21, and the second pipe 22. Also, the heater 63 is kept OFF. In such a state, while the catalyst C is set in the catalyst container 62, no sample S (soil containing the target substance) is set in the sample container 61.

The concentration sensor 26 housed in the detection chamber 27 detects the concentration of carbon dioxide in the gas brought into the detection chamber 27.

The control unit 40 stores the value detected by the concentration sensor 26 during the background measurement process 81 in the storage medium 44 as a background measurement value 81D.

<Discharging Process>

The control unit 40 switches the heater 63 from OFF to ON. As a result, the catalyst C set in the catalyst container 62 is heated to a predetermined temperature. The temperature of the catalyst C is therefore kept substantially constant. Although it depends on a type of the catalyst C, the temperature of the catalyst C during the discharging process 82 is in a range between 200° C. and 300° C., for example. The concentration sensor 26 housed in the detection chamber 27 detects the concentration of carbon dioxide contained in the gas in the detection chamber 27.

<Main Measurement Process>

Figure 2:
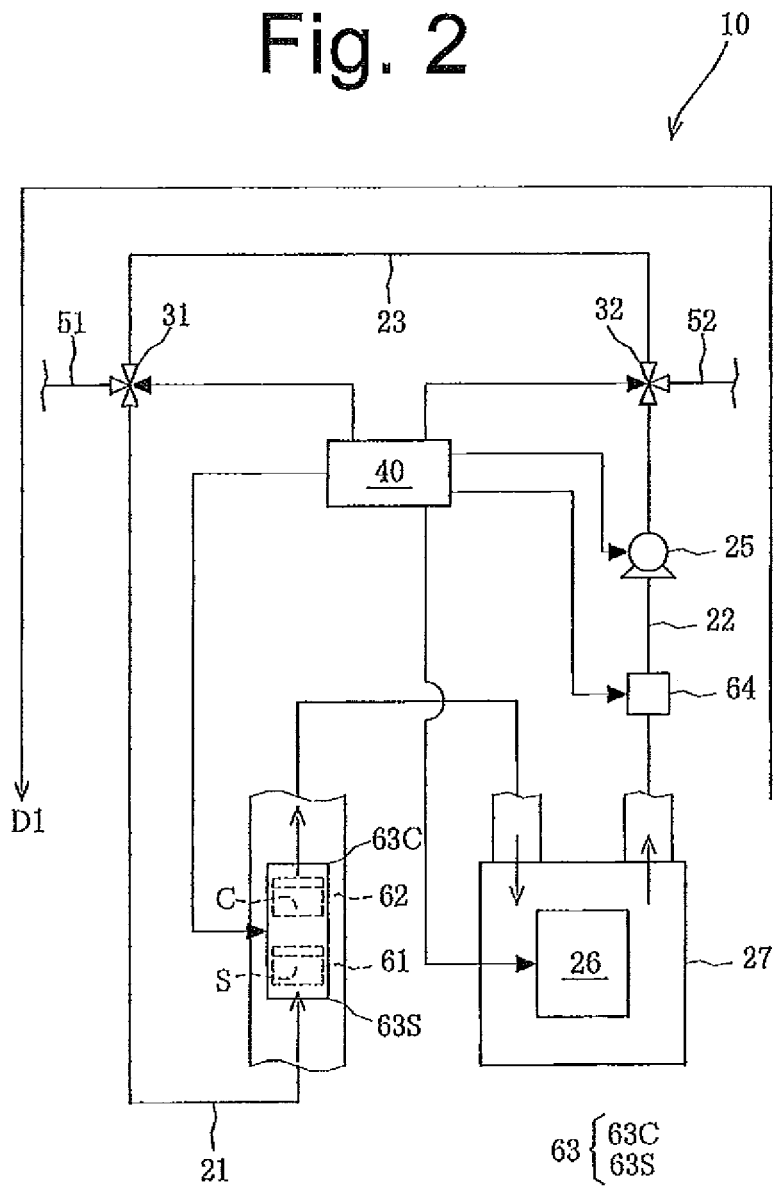
FIG. 2 is an explanatory diagram showing an outline of the first concentration measuring device with the pipes set in a circulation state.

First, the control unit 40 controls the first and second three-way valves 31 and 32 so as to set the first to third pipes 21 to 23 to the circulation state (see FIG. 2, denoted as "B" in FIG. 5B). As a result, the first to third pipes 21 to 23 together form the circulation path closed off from the outside air.

Next, the sample S is set in the sample container 61. Thereafter, the sample container 61 is fixed in the first pipe 21 by means of the sample container holder 70. The sample S set in the sample container 61 is thereby heated to a predetermined temperature. The temperatures of the catalyst C and the sample S are therefore kept substantially constant. The target substance contained in the sample S is vaporized by heating the sample S. Also, when the vaporized target substance comes into contact with the catalyst C, the vaporized target substance is combusted, thereby generating carbon dioxide in an amount corresponding to the amount of the target substance. Preferably, the heating temperature for the sample S and the catalyst C during the main measurement process 83 is substantially the same as the heating temperature for the catalyst C during the discharging process 82. It may be in a range between 200° C. and 300° C., for example.

The concentration sensor 26 housed in the detection chamber 27 detects the concentration of carbon dioxide contained in the gas in the detection chamber 27. Note that the detection of carbon dioxide concentrations by means of the concentration sensor 26 is preferably performed in a continuous manner.

The control unit 40 stores the value detected by the concentration sensor 26 in the main measurement process 83 in the storage medium 44 as a main measurement value 83D.

<Cooling Process>

The control unit 40 controls the first and second three-way valves 31 and 32 so as to switch over to the air intake and exhaust state (see FIG. 1). As a result, outside air is directly discharged from the exhaust pipe 52 after passing through the intake pipe 51, the first pipe 21, and the second pipe 22. Furthermore, the control unit 40 switches the heater 63 from ON to OFF. Therefore, fresh outside air is continuously introduced to the sample container 61 during the cooling process 84. As a result, the sample S held in the sample container 61 and the catalyst C held in the catalyst container 62 are cooled. After the sample S is cooled to a certain temperature, the sample or the catalyst C can be taken out to the outside.

Note that an exhaust pump 28 for discharging the gas inside the detection chamber 27 to the outside may be provided in the detection chamber 27. The operation of the exhaust pump 28 can improve the efficiency of the cooling process.

In a case where only the sample S is replaced with another, the control unit 40 may turn off the sample heater 63S while operating the catalyst heater 63C. Specifically, the control unit 40 may turn off the sample heater 63S while operating the catalyst heater 63C during a period ranging from a point in time before the replacement operation of the sample S to a point in time after the replacement operation of the sample S.

Note that the control unit 40 may store a value detected by the concentration sensor 26 in the cooling process 84 in the storage medium 44 as a cooling process measurement value 84D.

Data Calculation Process>

In the data calculation process, the control unit 40 performs predetermined calculations using the data 81O to 84D and the like. The data calculation process may be performed in the middle of the concentration measuring method or after the concentration measuring method. Examples of major calculations performed by the control unit 40 may include: a calculation for a test substance production amount which calculates a difference 83X between the initial data and the final data of the main measurement values 83D; a calculation for a target substance amount which calculates the amount of the target substance based on the result of the calculation for the test substance production amount; and an offset calculation which subtracts the background measurement value 81D from the main measurement value 83D.

As described above, the main measurement process 83 is performed in the concentration measuring method performed by the concentration measuring device 10. In the main measurement process 83, the gas having passed through the detection chamber 27 passes through the third pipe 23 and again through the first pipe 21, i.e., through the sample container 61 and the catalyst container 62 in this order due to the circulation state (see FIG. 2) of the first to third pipes 21 to 23. When the gas having passed through the detection chamber 27 passes through the sample container 61 and the catalyst container 62 again, a target substance is newly vaporized from the sample container 61. Furthermore, the newly-vaporized target substance is combusted in the catalyst container 62, thereby producing carbon dioxide in an amount corresponding to the amount of the target substance. Thus, the gas again introduced into the detection chamber 27 contains the previously-generated carbon dioxide and the newly-generated carbon dioxide. Therefore, the concentration of the carbon dioxide contained in the gas again introduced into the detection chamber 27 increases as the number of gas circulations increases. Thus, the concentration of carbon dioxide contained in the gas can be detected easily and reliably without performing elaborate flow rate control by means of the pump 25.

As described above, the concentration measuring device 10 includes: the first to third pipes 21 to 23 together forming the circulation path; the pump 25 for flowing a gas in the predetermined circulating direction in the circulation path; the sample container 61 provided in the circulation path, for holding the sample S therein; and the concentration sensor 26 for measuring a concentration of a target substance from the sample S. Thus, the concentration of the target substance from the sample S can be measured easily and reliably without performing elaborate flow rate control by means of the pump 25. Furthermore, by continuously recording the detection results from the concentration sensor 26, it becomes possible to know a history for the amounts of the target substance obtained from the sample S.

It is desirable to perform the main measurement process 83 until the detected value from the concentration sensor 26 becomes saturated. If the main measurement process 83 is performed until the detected value from the concentration sensor 26 becomes saturated, however, an amount of time required for the main measurement process 83 becomes longer. Therefore, the main measurement process 83 may be performed only within a predetermined amount of time. Even if the main measurement process 83 is terminated before the detected value from the concentration sensor 26 becomes saturated as just described, a relative evaluation among a plurality of samples can be obtained by employing the same processing time 83T in the main measurement process 83 for the plurality of samples.

In the concentration measuring method, the background measurement process 81 is performed prior to the main measurement process 83. The background measurement value 81D obtained by the background measurement process 81 is a value representing a concentration of carbon dioxide contained in outside air. Therefore, if the control unit 40 performs the offset calculation of subtracting the background measurement value 81D from the main measurement value 83D, it becomes possible to compare experimental data having different outside air conditions with each other.

Furthermore, in the discharging process 82, carbon dioxide adsorbed onto the catalyst C from the beginning can be discharged by heating the catalyst C. Therefore, the concentration of the carbon dioxide adsorbed onto the catalyst C from the beginning, which is the cause of a noise, can be eliminated from the measured data in the main measurement process 83. Here, the discharging process 82 is preferably continued until no carbon dioxide is emitted from the catalyst C.

The control unit 40 may store a value detected by the concentration sensor 26 during the discharging process 82 in the storage medium 44 as a discharging process measurement value 82D. The discharging process measurement value 82D can be utilized as follows. Indexes regarding the adsorption ability of the catalyst C to be used are stored in the storage medium 44 of the control unit 40 in advance. Such an index is appropriately determined for each of conditions such as an adsorption amount of carbon dioxide at a predetermined temperature and within a predetermined elapsed time, an amount of time that elapses before the adsorption of carbon dioxide starts at the predetermined temperature, and a temperature that reaches before the adsorption of carbon dioxide starts within the predetermined elapsed time. In order to make the catalyst C adsorb carbon dioxide thereonto, the catalyst C is exposed to carbon dioxide under such conditions. Thereafter, the catalyst container 62 housing the catalyst C therein is fixed in the first pipe 21.

The concentration measuring method is performed next. According to this concentration measuring method, after the discharging process 82, i.e., between the discharging process 82 and the main measurement process 83, the control unit 40 determines whether or not a value obtained from the discharging process measurement value 82D (for example, an integrated value of the carbon dioxide concentration or a maximum value of the carbon dioxide concentration) satisfies the index of the catalyst C stored in advance. If it is determined that the value satisfies the index of the catalyst C, the control unit 40 concludes that the catalyst C associated with that discharging process measurement value 82D has a predetermined adsorption ability. On the other hand, if it is determined that the value does not satisfy the index of the catalyst C, the control unit 40 concludes that the catalyst C associated with that discharging process measurement value 82D has no predetermined adsorption ability. Therefore, the catalyst C unknown about its adsorption ability can be determined whether to have the predetermined adsorption ability and the main measurement process 83 can be performed only on the catalyst C having the predetermined adsorption ability.

Here, the control unit 40 may perform a calculation to obtain an average concentration value $81X_{AV}$ from the background measurement value 81D. Furthermore, with a value obtained by adding a predetermined reference value Y to the average concentration value $81X_{AV}$ obtained from the background measurement value 81D used as a threshold value, the control unit 40 may determine whether or not the discharging process measurement value 82D is greater than the threshold value. Furthermore, if it is determined that the discharging process measurement value 82D is equal to the threshold value, the control unit 40 may terminate the discharging process 82. This makes it possible for the control unit 40 to determine a termination condition for the discharging process 82 on the basis of the discharging process measurement value 82D.

Although the background measurement process 81 and the discharging process 82 are performed in this order in the above-described embodiment, the present invention is not limited thereto. The discharging process 82 and the background measurement process 81 may be performed in this order. However, from the perspective that an amount of time during which the heater 63 is ON is reduced and the termination condition for the discharging process 82 can be determined on the basis of the discharging process measurement value 82D, it is better to perform the background measurement process 81 and the discharging process 82 in this order.

The first and second three-way valves 31 and 32 function as the switching mechanism for switching the first to third pipes 21 to 23 between the air intake and exhaust state and the circulation state and also as a cooling mechanism for cooling the sample S or the catalyst C after the main measurement process 83. Thus, there is no need to separately provide a cooling device for cooling the sample S.

Figure 6A:
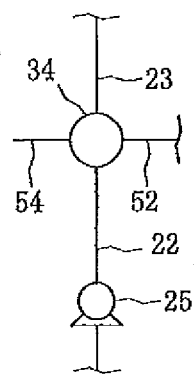
FIG. 6A is an explanatory diagram showing an outline of a four-way valve.
Figure 6B:
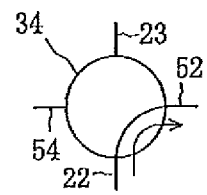
FIGS. 6B to 6D are each an explanatory diagram showing a state of the four-way valve.
Figure 6C:
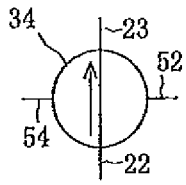
Figure 6D:
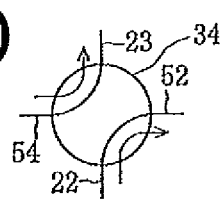

As shown in FIG. 6A, a four-way valve 34 including a function of an open valve 23B may be provided as a substitute for the second three-way valve 32. The four-way valve 34 also connects with an exhaust pipe 54 in addition to the second pipe 22, the third pipe 23, and the exhaust pipe 52. The four-way valve 34 can change the path among a first open state (see FIG. 6B) in which the second pipe 22 is opened to the outside and the third pipe 23 and the exhaust pipe 54 are closed off from the outside, a closed state (see FIG. 6C) in which the circulation path established by the first to third pipes 21 to 23 is closed off from the outside, and a second open state (see FIG. 6D) in which the second pipe 22 is opened to the outside via the exhaust pipe 52 and an open end of the third pipe 23 is opened to the outside via the exhaust pipe 54.

By changing the first three-way valve 31 to the open state and changing the four-way valve 34 to the second open state (see FIG. 6D), a gas in the third pipe 23 can be discharged into outside air and outside air can be introduced into the third pipe 23. Thus, the gas containing carbon dioxide generated upon the measurement can be discharged into outside air from the third pipe 23.

Although the exhaust pipe 54 is provided for the purpose of illustration, the exhaust pipe 54 may be omitted. The valve of the four-way valve 34 directly connected to the exhaust pipe 54 may be opened to the outside directly.

Figure 7A:
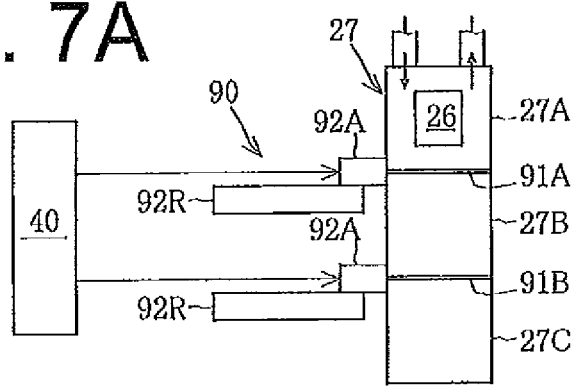
FIGS. 7A to 7C are each an explanatory diagram showing a state of first and second partition plates and a partition plate drive mechanism.
Figure 7B:
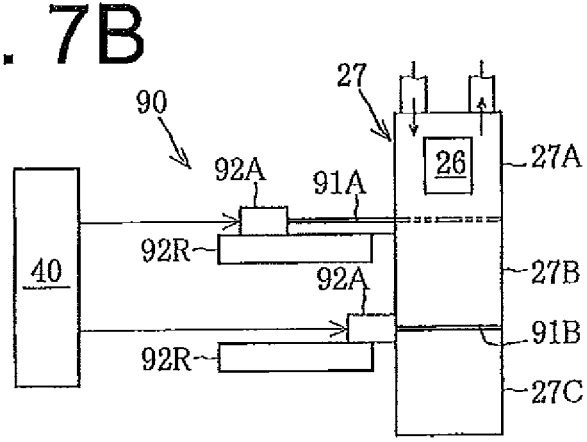
Figure 7C:
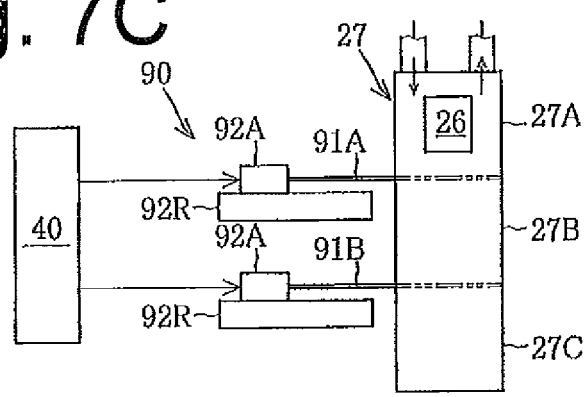

As shown in FIGS. 7A to 7C, the concentration measuring device 10 may include: first and second partition plates 91A and 91B for dividing the detection chamber 27 into independent spaces (first to third chambers 27A to 27C); and a partition plate drive mechanism 92 for individually driving the first and second partition plates 91A and 91B.

The first partition plate 91A is provided to open and close a portion between the first chamber 27A and the second chamber 27B. The first partition plate 91A is movable between a first dividing position at which the first chamber 27A and the second chamber 27B are separated from each other and a first retracted position retracted from the first dividing position. The second partition plate 91B is provided to open and close a portion between the second chamber 27B and the third chamber 27C. The second partition plate 91B is movable between a second dividing position for dividing the detection chamber 27 and a second retracted position retracted from the second dividing position. The concentration sensor 26 is provided in the first chamber 27A that is always in communication with the first and second pipes 21 and 22.

The partition plate drive mechanism 92 individually moves the first and second partition plates 91A and 91B between the respective dividing positions and the respective retracted positions. The partition plate drive mechanism 92 includes a connector 92A connected to each of the first and second partition plates 91A and 91B; a rail 92R provided for the connector 92A; and a slide device 92S for sliding the connector 92A along the rail 92R. The control unit 40 causes the partition plate drive mechanism 92 to individually moves the first and second partition plates 91A and 91B between the respective dividing positions and the respective retracted positions.

Functions of the first and second partition plates 91A and 91B and the partition plate drive mechanism 92 will now be described below.

Before the background measurement process 81 is performed, the control unit 40 first sets the first partition plate 91A at the first retracted position and sets the second partition plate 91B at the second dividing position as shown in FIG. 7B.

Figure 8A:
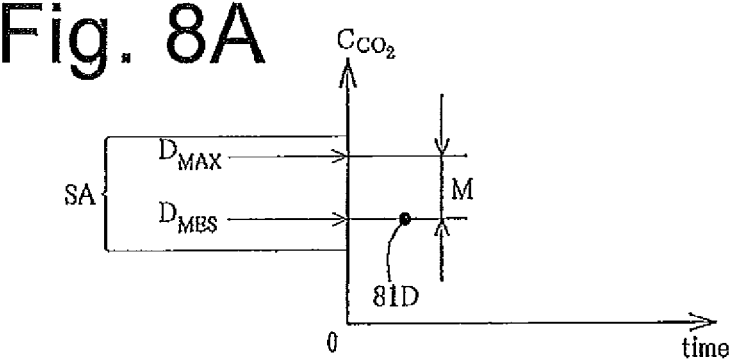
FIGS. 8A to 8C are each a graph showing a transition of detected values from the concentration sensor when a background measurement process 81 is started, with the vertical axis thereof indicating a concentration of carbon dioxide detected by the concentration sensor and the horizontal axis thereof indicating time.

In the background measurement process 81 (see FIG. 5A), the control unit 40 stores a sensing signal from the concentration sensor 26 in the RAM 42 as a measured value $D_{MES}$ at a concentration shown in FIG. 8A.

Next, the control unit 40 adds the measured value $D_{MES}$ at the concentration to a concentration margin M stored in the storage medium 44 in advance to calculate a maximum value $D_{MAX}$ for the concentration in this measurement. The control unit 40 then stores the maximum value $D_{MAX}$ for the concentration in the RAM 42. Thereafter, the control unit 40 refers to a concentration detection range SA of the concentration sensor 26 stored in the storage medium 44 in advance so that it is determined whether or not both of the measured value $D_{MES}$ at the concentration and the maximum value $D_{MAX}$ for the concentration are within the detection range SA.

If it is determined that the both are within the detection range SA (see FIG. 8A), the control unit 40 leaves the first and second partition plates 91A and 91B as they are and performs the following processes 82 to 84.

Figure 8B:
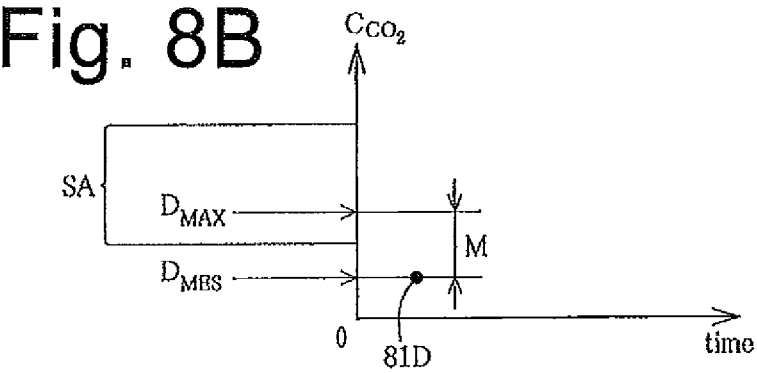

If it is determined that both of them are not within the detection range SA, the control unit 40 causes the first and second partition plates 91A and 91B to be moved as follows. If the measured value $D_{MES}$ at the concentration is smaller than the minimum value of the detection range SA (see FIG. 8B, the control unit 40 causes the first partition plate 91A to be moved from the first retracted position to the first dividing position. As a result of the movement, the volume of the detection chamber 27 in communication with the first and second pipes 21 and 22 is reduced, and accordingly, the concentration of carbon dioxide in the detection chamber 27 is increased. Therefore, both of the measured value $D_{MES}$ at the concentration and the maximum value $D_{MAX}$ for the concentration can fall within the detection range SA (see FIG. 8A).

Similarly, if the maximum value $D_{MAX}$ for the concentration is greater than the maximum value of the detection range SA, the control unit 40 causes the second partition plate 91B to be moved from the second dividing position to the second retracted position. As a result of the movement, the volume of the detection chamber 27 in communication with the first and second pipes 21 and 22 is reduced, and accordingly, the concentration of carbon dioxide in the detection chamber 27 is decreased. Therefore, both of the measured value $D_{MES}$ at the concentration and the maximum value $D_{MAX}$ for the concentration can fall within the detection range SA.

With the use of the first and second partition plates 91A and 91B and the partition plate drive mechanism 92 as just described, the processes 81 to 84 can be performed with both of the measured value $D_{MES}$ at the concentration and the maximum value $D_{MAX}$ for the concentration falling within the detection range SA.

Although the concentration sensor 26 is provided in the detection chamber 27 in the above-described embodiment, the present invention is not limited thereto. A position at which the concentration sensor 26 is provided may be in the first pipe 21 or the second pipe 22 as long as it is located downstream of the catalyst container 62.

Figure 9A:
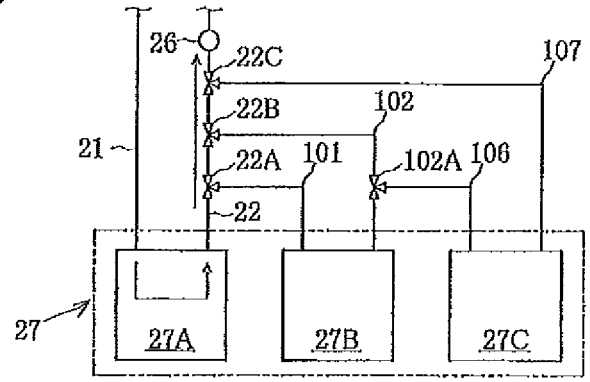
FIGS. 9A to 9C are each an explanatory diagram showing a state of a flow path changing mechanism.
Figure 9B:
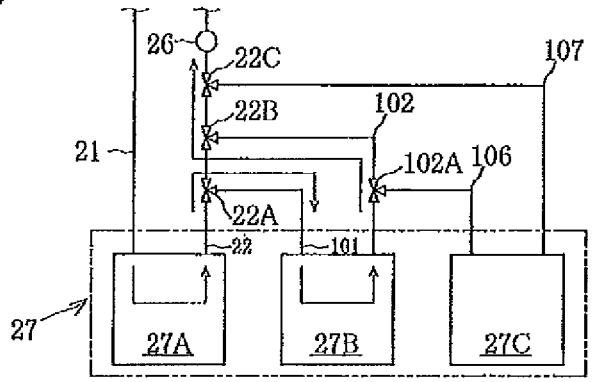
Figure 9C:
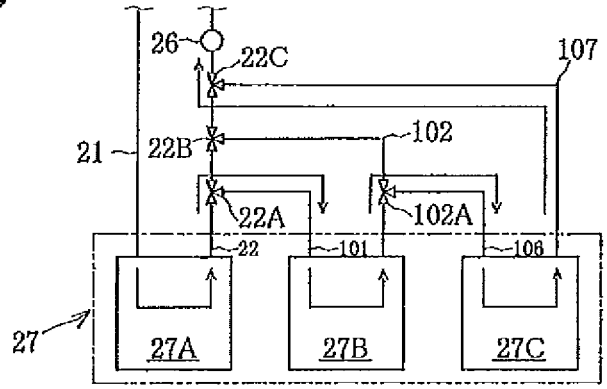

Furthermore, as shown in FIGS. 9A to 9C, the concentration sensor 26 may be provided in the second pipe 22 and then the detection chamber 27 may be divided into three first to third detection chambers 27A to 27C in the concentration measuring device 10. The concentration measuring device 10 also includes a flow path changing mechanism.

The flow path changing mechanism includes: three-way valves 22A to 22C and 102A; and pipes 101, 102, 106, and 107. The three-way valves 22A to 22C are arranged in this order from the upstream side to the downstream side. The three-way valves 22A to 22C are provided in the second pipe 22 between the first detection chamber 27A and the concentration sensor 26. The pipe 101 connects between the three-way valve 22A and the second detection chamber 27B. The pipe 102 connects between the three-way valve 22B and the second detection chamber 27B. Also, the three-way valve 102A is provided in the pipe 102. The pipe 106 connects between the three-way valve 102A and the third detection chamber 27C. The pipe 107 connects between the third detection chamber 270 and the three-way valve 22C. The control unit 40 (see FIG. 1, for example) controls the three-way valves 22A to 220 and 102A individually.

The control unit 40 controls the three-way valves 22A to 22C and 102A, so that the flow path changing mechanism can change the state of the path among a first state (see FIG. 9A) in which a gas having passed through the first detection chamber 27A directly passes through the second pipe 22, a second state (see FIG. 9B) in which a gas having passed through the first detection chamber 27A passes through the second detection chamber 27B and then returns to the second pipe 22, and a third state (see FIG. 9C) in which a gas having passed through the first detection chamber 27A passes through the second detection chamber 27B and the third detection chamber 270 and then returns to the second pipe 22.

Functions of the flow path changing mechanism will now be described.

Before the background measurement process 81 is performed, the control unit 40 first controls the flow path changing mechanism to be set to the second state (see FIG. 9B). In the background measurement process 81 (see FIG. 5A), the control unit 40 stores a sensing signal from the concentration sensor 26 in the RAM 42 as a measured value $D_{MES}$ at a concentration shown in FIG. 8A. Next, the control unit 40 adds the measured value $D_{MES}$ at the concentration to a concentration margin M stored in the storage medium 44 in advance to calculate a maximum value $D_{MAX}$ for the concentration in this measurement. The control unit 40 then stores the maximum value $D_{MAX}$ for the concentration in the RAM 42. Thereafter, the control unit 40 refers to a concentration detection range SA of the concentration sensor 26 stored in the storage medium 44 in advance, so that it is determined whether or not both of the measured value $D_{MES}$ at the concentration and the maximum value $N_{MAX}$ for the concentration are within the detection range SA.

If it is determined that the both are within the detection range SA (see FIG. 8A), the control unit 40 leaves the flow path changing mechanism as it is and performs the following processes 82 to 84.

Figure 8C:
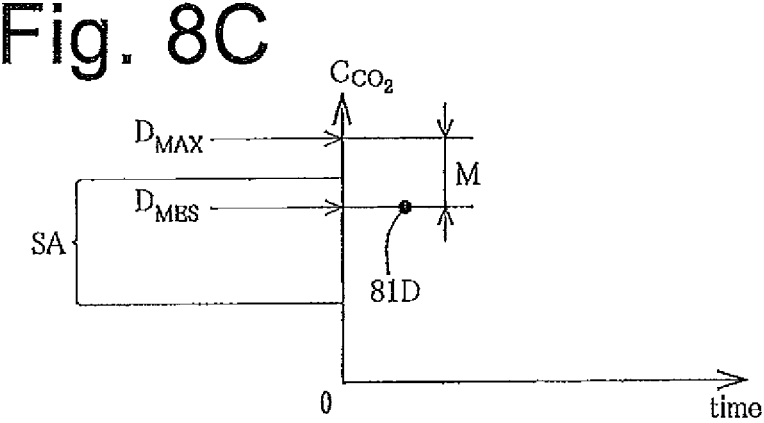

If it is determined that both of them are not within the detection range SA, the control unit 40 changes the state of the flow path changing mechanism as follows. If the measured value $D_{MES}$ at the concentration is smaller than the minimum value of the detection range SA (see FIG. 8B), the control unit 40 operates the three-way valves 22A and 22B to set the flow path changing mechanism to the first state (see FIG. 9A). As a result of the operation, the volume of a flow path through which the gas flows is thereby reduced, resulting in an increase in the concentration of carbon dioxide in the flow path. Therefore, both of the measured value $D_{MES}$ at the concentration and the maximum value $D_{MAX}$ for the concentration can fall within the detection range SA (see FIG. 8A). Similarly, if the maximum value $D_{MAX}$ for the concentration is greater than the maximum value of the detection range SA (see FIG. 8C), the control unit 40 controls the three-way valves 22C and 102A to be set to the third state (see FIG. 9C). As a result of the operation, the volume of a flow path through which the gas flows is thereby increased, resulting in a decrease in the concentration of carbon dioxide in the flow path. Therefore, both of the measured value $D_{MES}$ at the concentration and the maximum value $D_{MAX}$ for the concentration can fall within the detection range SA (see FIG. 8A).

With the use of the flow path changing mechanism as just described, the processes 81 to 84 can be performed with both of the measured value $D_{MES}$ at the concentration and the maximum value $D_{MAX}$ for the concentration falling within the detection range SA.

When a flow rate value based on a sensing signal from the flow sensor 64 does not come closer to a target value even by the control of the pump 25 by the control unit 40, it is likely to be due to a failure of the pump 25 or the flow sensor 64. Thus, a failure of the pump 25 or the flow sensor 64 can be detected by controlling the pump 25 on the basis of a sensing signal from the flow sensor 64. An example of a procedure for detecting a failure of the pump 25 or the flow sensor 64 is as follows.

First, the control unit 40 reads a sensing signal from the flow sensor 64. Based on a conversion formula stored in the storage medium 44 or the like, a flow rate value is obtained from the read sensing signal. The converted flow rate value is stored in the RAM 42 as a first flow rate value. Second, the control unit 40 reads a target value stored in advance from the RAM 42. Third, the control unit 40 compares the flow rate value based on the sensing signal from the flow sensor 64 with the target value to determine whether or not the both are equal to each other. Fourth, in a case where it is determined that the both are equal to each other, the control unit 40 does not change the drive condition on the pump 25. If it is determined that the both are different from each other, on the other hand, the control unit 40 changes the drive condition on the pump 25 so that the flow rate value based on the sensing signal from the flow sensor 64 becomes equal to the desired flow rate value.

Thereafter, the control unit 40 reads the sensing signal from the flow sensor 64 and stores a flow rate value based on this signal in the RAM 42 as a second flow rate value. Here, the control unit 40 determines which of the first flow rate value and the second flow rate value is closer to the target value. If the second flow rate value is closer to the target value than the first flow rate value, the control unit 40 concludes it as normal. If the first flow rate value is closer to the target value than the second flow rate value, the control unit 40 concludes it as abnormal. When it is concluded as abnormal, the control unit 40 may output a warning via the output device 46 or the like.

The cooling process measurement value 84D may be utilized as follows. First, during a cooling process, the control unit 40 refers to the background measurement value 81D (for example, the average concentration value $81X_{AV}$), so that it is determined whether or not the latest detected value of the cooling process measurement values 84D associated with this cooling process is approximately equal to the background measurement value 81D referred to by comparison. If it is determined that they are substantially the same, the control unit 40 terminates the cooling process immediately. If it is determined that they are not substantially the same, on the other hand, the control unit 40 concludes it as abnormal. When it is concluded as abnormal, the control unit 40 may output a warning via the output device 46 or the like.

As described above, the presence or absence of malfunction in the valves and sensors provided in the concentration measuring device 10 can be detected in a simple manner in the concentration measuring method performed by the concentration measuring device 10.

Although the flow rate of the gas flowing through the second pipe 22 is kept constant by means of the flow sensor 64 in the above-described embodiments, the present invention is not limited thereto. The flow sensor 64 may be omitted.

Concentration measuring devices 110 and 210, which are modifications of the above-described embodiment (the concentration measuring device 10), will now be described below. Only those different from the above-described embodiment will be described elements identical to those in the above-described embodiment will be denoted by the same reference numerals and the detailed description thereof will be omitted.

Figure 10:
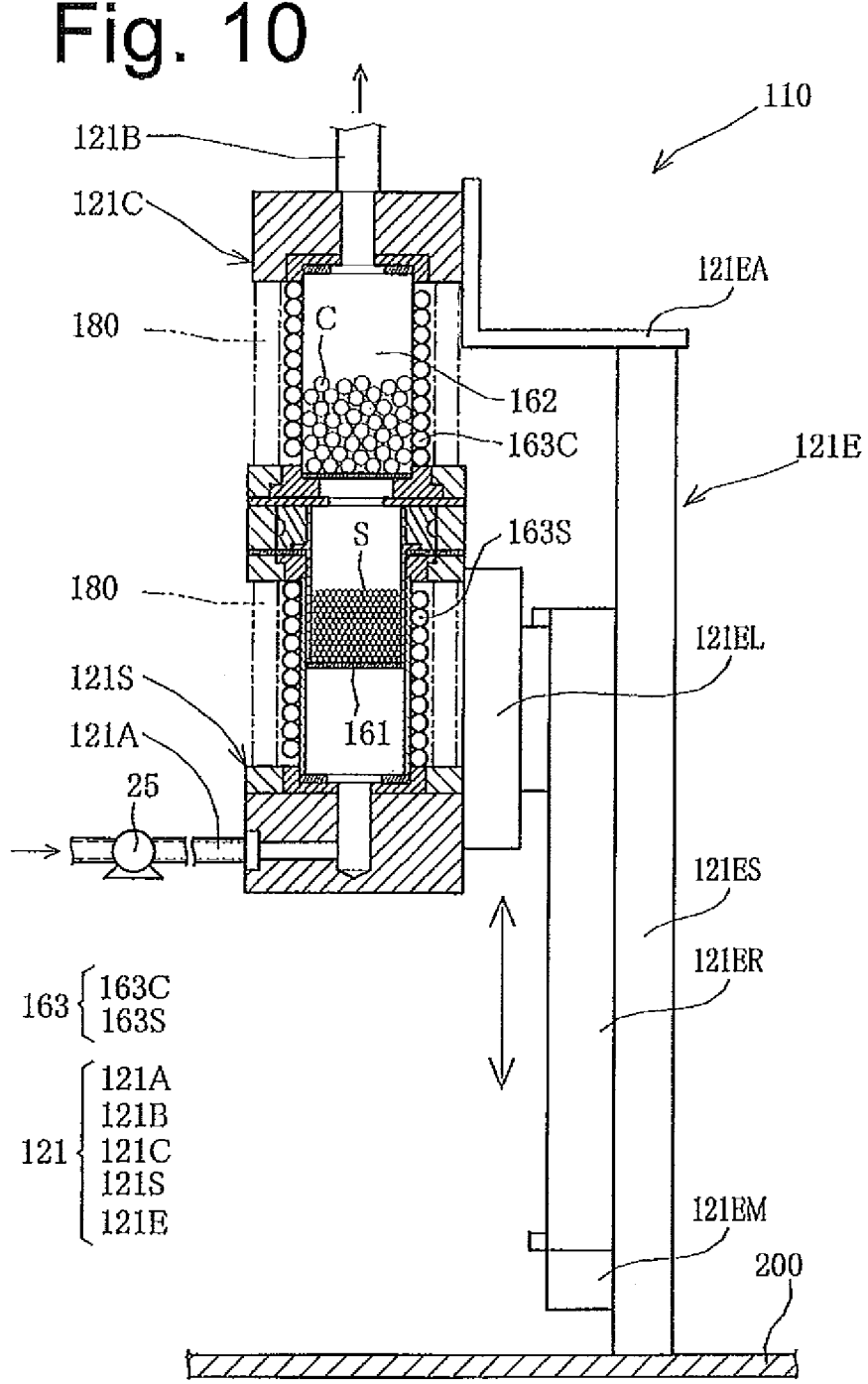
FIG. 10 is an explanatory diagram showing, in an enlarged manner, an essential part of a second concentration measuring device in a contact state.

As shown in FIG. 10, the concentration measuring device 110 includes: a first pipe 121; a sample container 161; a catalyst container 162; and a heater 163 in place of the first pipe 21, the sample container 61, the catalyst container 62, and the heater 63 in the concentration measuring device 10 shown in FIG. 1.

The first pipe 121 includes: a flexible hose 121A; a heat-resistant tube 121B; a catalyst container holder 121O for holding the catalyst container 162; a sample container holder 121S for holding the sample container 161; and a position switching mechanism 121E for switching a relative position between the sample container holder 121S and the catalyst container holder 121C. The flexible hose 121A is connected to an air supply port of the pump 25.

Figure 11:
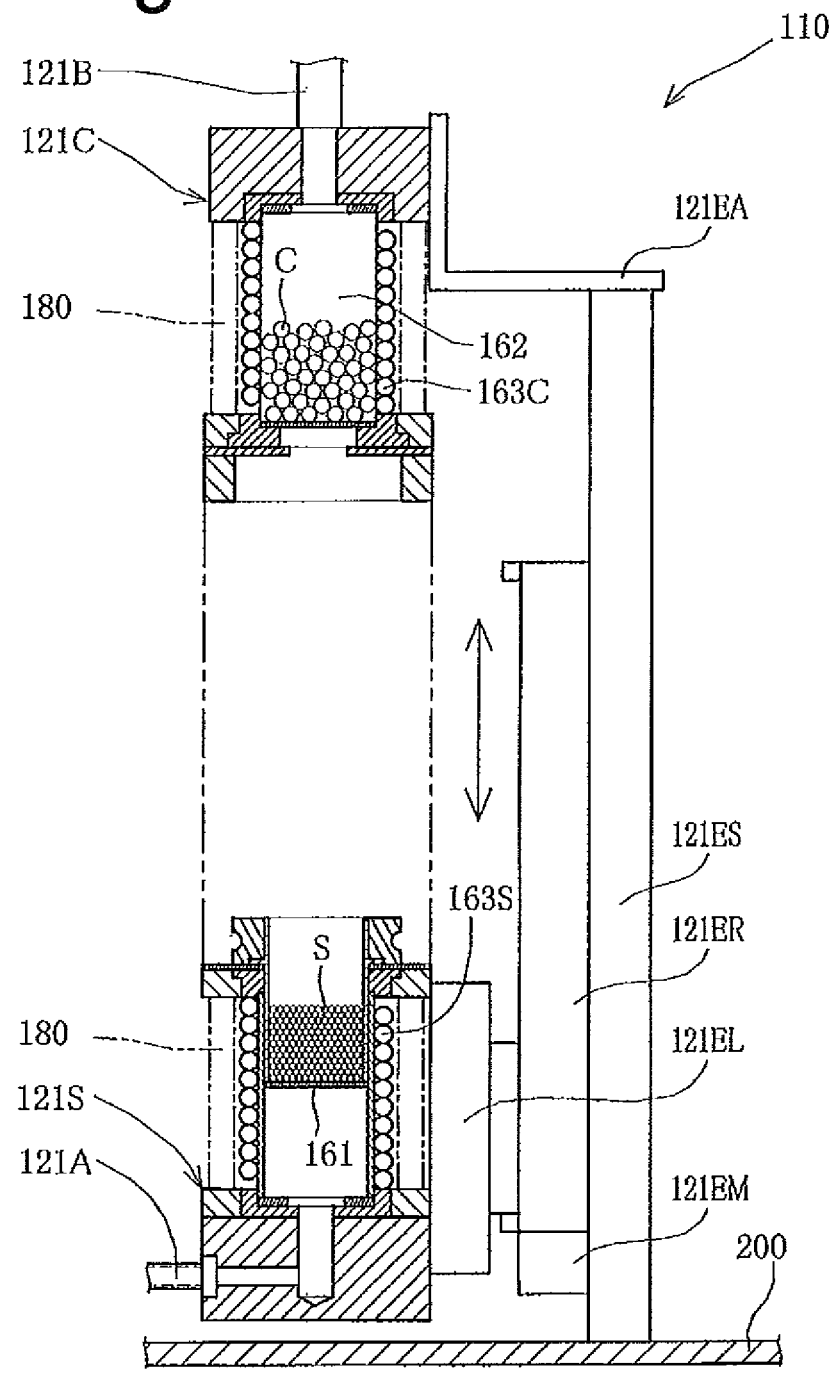
FIG. 11 is an explanatory diagram showing, in an enlarged manner, the essential part of the second concentration measuring device in a separated state.
Figure 12:
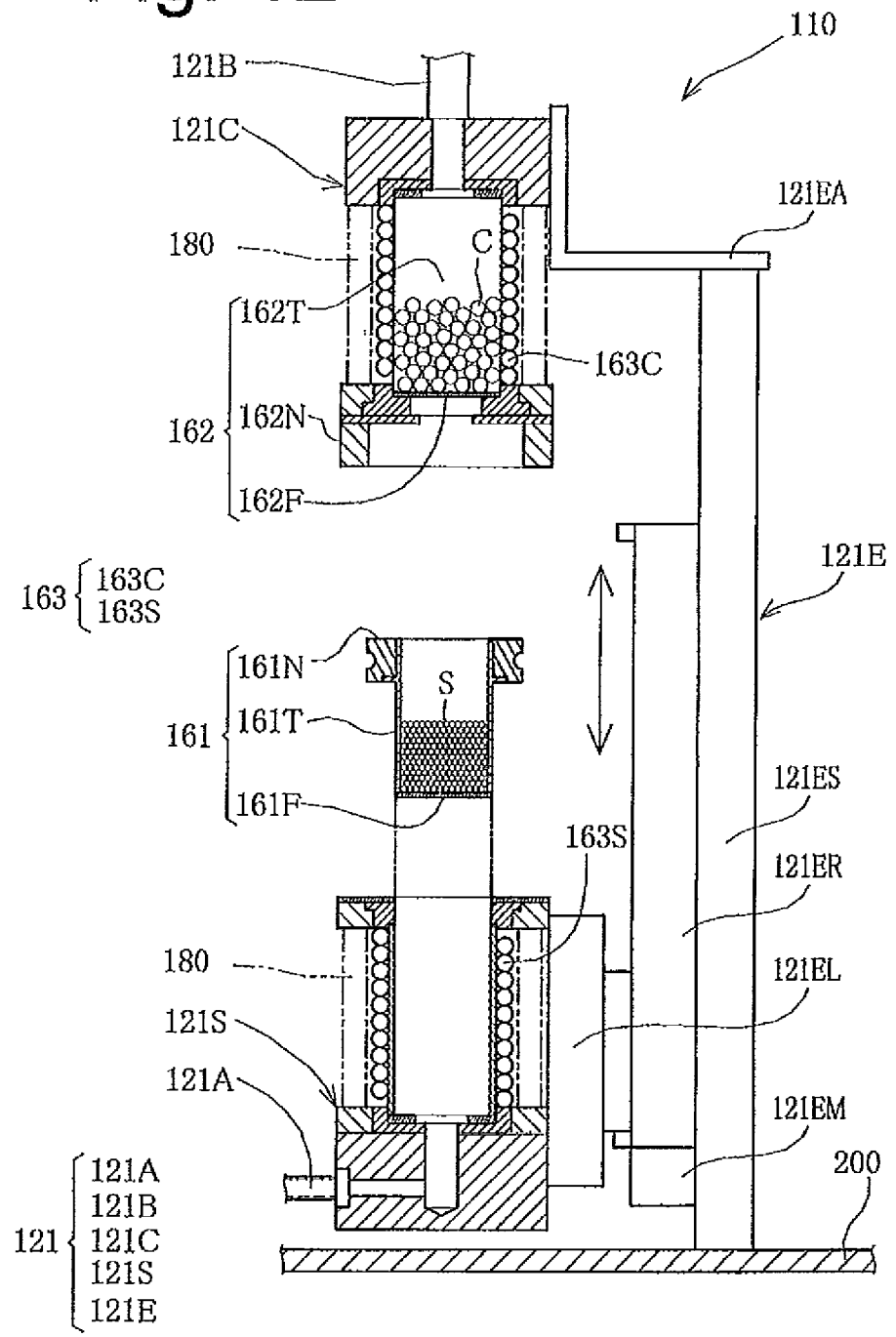
FIG. 12 is an explanatory diagram showing an outline of a sample container capable of being attached to or detached from a sample container holder.

As shown in FIGS. 11 and 12, the sample container 161 is detachably attached to the sample container holder 121S. The sample container 161 includes: a sample-side cylindrical portion 161T provided in a standing position with both ends thereof being opened; a sample-side bottom filter 161F provided at the lower-side opening of the sample-side cylindrical portion 161T; and a sample-side insulating member 161N provided around the periphery of the upper-side opening of the sample-side cylindrical portion 161T.

The catalyst container 162 is detachably attached to the catalyst container holder 121O. The catalyst container 162 includes: a catalyst-side cylindrical portion 162T provided in a standing position with both ends thereof being opened; a catalyst-side bottom filter 162F provided at the lower-side opening of the catalyst-side cylindrical portion 162T; and a catalyst-side insulating member 162N provided around the periphery of the lower-side opening of the catalyst-side cylindrical portion 162T. A bottom portion of the catalyst-side insulating member 162N is provided with a recess having a shape into which the sample-side insulating member 161N can be fitted.

The position switching mechanism 121E includes: a stand 121ES fixed to a chassis 200; a rail 121ER provided on the stand 121ES so as to extend in the vertical direction; a slide member 121EL capable of moving in the vertical direction along the rail 121ER while holding the sample container holder 121S; an angle 121EA fixed to a portion of the stand 121ES positioned higher than the rail 121ER, for holding the catalyst container 162; and a motor 121EM for driving the slide member 121EL.

Because the position switching mechanism 121E has the slide member 121EL, the sample container holder 121S and the catalyst container holder 121C can be switched between a separated state (see FIG. 11) in which they are separated from each other and a contact state (see FIG. 10) in which they are in contact with each other. In the contact state, the bottom portion of the catalyst-side insulating member 162N is fitted with the sample-side insulating member 161N, thereby allowing the flexible hose 121A and the heat-resistant tube 121B to be communicated with each other via the sample container 161 and the catalyst container 162. In the separated state, on the other hand, the sample container 161 and the catalyst container 162 are each opened to the external space (see FIG. 11).

The heater 163 includes: a sample heater 163S and a catalyst heater 163C. The sample heater 163S is a coil heater provided helically along the circumference of the sample container holder 121S. The catalyst heater 163C is a coil heater provided helically along the circumference of the catalyst container holder 121C. Under the control of the control unit 40, the sample heater 163S and the catalyst heater 163C independently perform the execution and stopping of the heating operation on the sample S and the execution and stopping of the heating operation on the catalyst C, respectively.

Moreover, a heat insulator 180 is preferably provided around the outer circumference of the sample heater 163S and around the outer circumference of the catalyst heater 163C.

A method for using the concentration measuring device 110 will now be described below.

When the motor 121EM is driven under the control of the control unit 40 (see FIG. 4), the sample container holder 121S slides along the rail 121ER. Due to the slide movement of the sample container holder 121S, the sample container holder 121S and the catalyst container holder 121C come into the separated state (see FIG. 11). In such a state, the sample container 161 can be attached to the sample container holder 121S or the catalyst container 162 can be attached to the catalyst container holder 121C (see FIG. 12).

Figure 13:
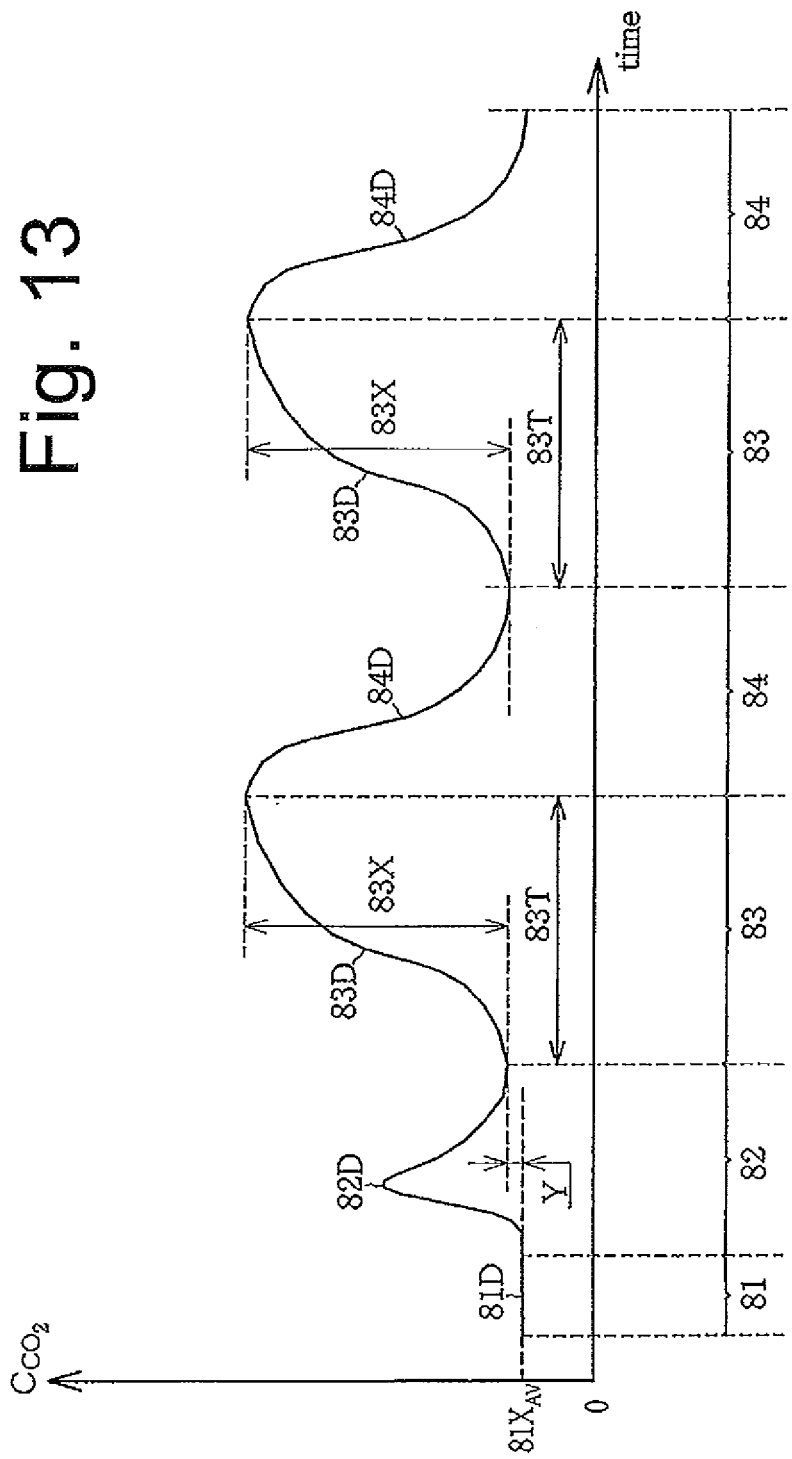
FIG. 13 a graph showing a transition of detected values from a concentration sensor in each of processes-when the second concentration measuring device is used, with the vertical axis thereof indicating a concentration of carbon dioxide detected by the concentration sensor and the horizontal axis thereof indicating time.

Next, the sample container holder 121S slides by the driving of the motor 121EM, thereby causing the sample container holder 121S and the catalyst container holder 121C to come into the contact state (see FIG. 10). In such a state, the concentration measuring device 110 can be switched between the air intake and exhaust state and the circulation state. In other words, in a case where the sample container holder 121B and the catalyst container holder 121C are in the contact state (see FIG. 10), the background measurement process 81 to the main measurement process 83 (see FIG. 13) can be performed sequentially. Also, the control unit 40 controls the heating operations of the catalyst heater 163C and the sample heater 163S in accordance with the contents of the background measurement process 81 to the main measurement process 83 (see FIG. 19). Herein, the "A" in FIG. 14 represents the air intake and exhaust state, and the "A" in FIG. 14 represents the circulation state. Specifically, the control unit 40 sets the heating operations of the sample heater 163B and the catalyst heater 163C to a stopped state in the background measurement process 81 as shown in FIG. 14. Then, the control unit 40 only performs the heating operation by means of the catalyst heater 163C in the discharging process 82. In the main measurement process 83, after setting the sample container 61 having the sample S therein to the contact state (see FIG. 10), the control unit 40 performs the heating operations of the sample heater 163S and the catalyst heater 163C.

In a case where the main measurement process 83 is performed following the cooling process 84 (see FIG. 13), the cooling process 84 and the subsequent processes are performed as follows.

In the cooling process 84, the control unit 40 controls the first and second three-way valves 31 and 32 to be switched to the air intake and exhaust state. As a result, the outside air passes through the first pipe 121, the second pipe 22, and the like, to be discharged into the outside air. Furthermore, in the cooling process 84, simultaneously with or after the switching to the air intake and exhaust state, the control unit 40 continues the heating operation of the catalyst heater 163C and stops the heating operation of the sample heater 163S. Additionally, in the cooling process 84, the control unit 40 switches the sample container holder 121S and the catalyst container holder 121C from the contact state (see FIG. 10) to the separated state (see FIG. 11) by means of the driving of the motor 121EM.

Subsequently, in the main measurement process 83, the sample container 161 is detached from the sample container holder 121S and the measured sample S is replaced with a new sample S. Furthermore, in the main measurement process 83, after setting the sample container 161 having the new sample S therein to the sample container holder 121B, the sample container holder 121B and the catalyst container holder 121C are switched from the separated state (see FIG. 11) to the contact state (see FIG. 10). Subsequently, in the main measurement process 83, the control unit 40 executes the heating operations of the sample heater 163B and the catalyst heater 163C. This will make it possible to perform the second main measurement process 83 (see FIG. 13) following the cooling process 84.

In a case where the main measurement process 83 is not performed following the cooling process 89, on the other hand, the control unit 40 only has to stop the heating operations of the sample heater 163B and the catalyst heater 163C simultaneously with or after the switching to the air intake and exhaust state in the cooling process 84 (see FIG. 14).

By individually controlling the heating operations of the sample heater 163S and the catalyst heater 163C as described above, the catalyst C can be prevented from being cooled during the replacement operation of the samples. Thus, in a case where the main measurement process 83 is performed on a plurality of samples 8, there is no need to perform the discharging process 82 one by one for the samples S. As a result, the main measurement process 83 can be efficiently performed on the plurality of samples S.

Although the catalyst container holder 121C is fixed and the sample container holder 121S is allowed for a slide movement in the above-described embodiment, the present invention is not limited thereto. The sample container holder 121B may be fixed and the catalyst container holder 121C may be allowed for a slide movement. Alternatively, the both holders 121C and 121S may be allowed for a slide movement.

Although the sample container holder 121S is moved along with the sample heater 163B in the above-described embodiment, the present invention is not limited thereto. Separately from the sample heater 163B, the sample container holder 121S may be independently movable. Alternatively, the sample container holder 121B may be fixed to the angle 121EA or the chassis 200.

Although the carbon dioxide concentration sensor is used as the concentration sensor 26 in the above-described embodiment, the present invention is not limited thereto. It may be any concentration sensor as long as it can measure a test substance.

In the above-described embodiment, when measuring a concentration of the petroleum-based hydrocarbon contained in the sample S, the reaction of the catalyst C generating carbon dioxide from the petroleum-based hydrocarbon is utilized. However, the present invention is not limited thereto.

Figure 15:
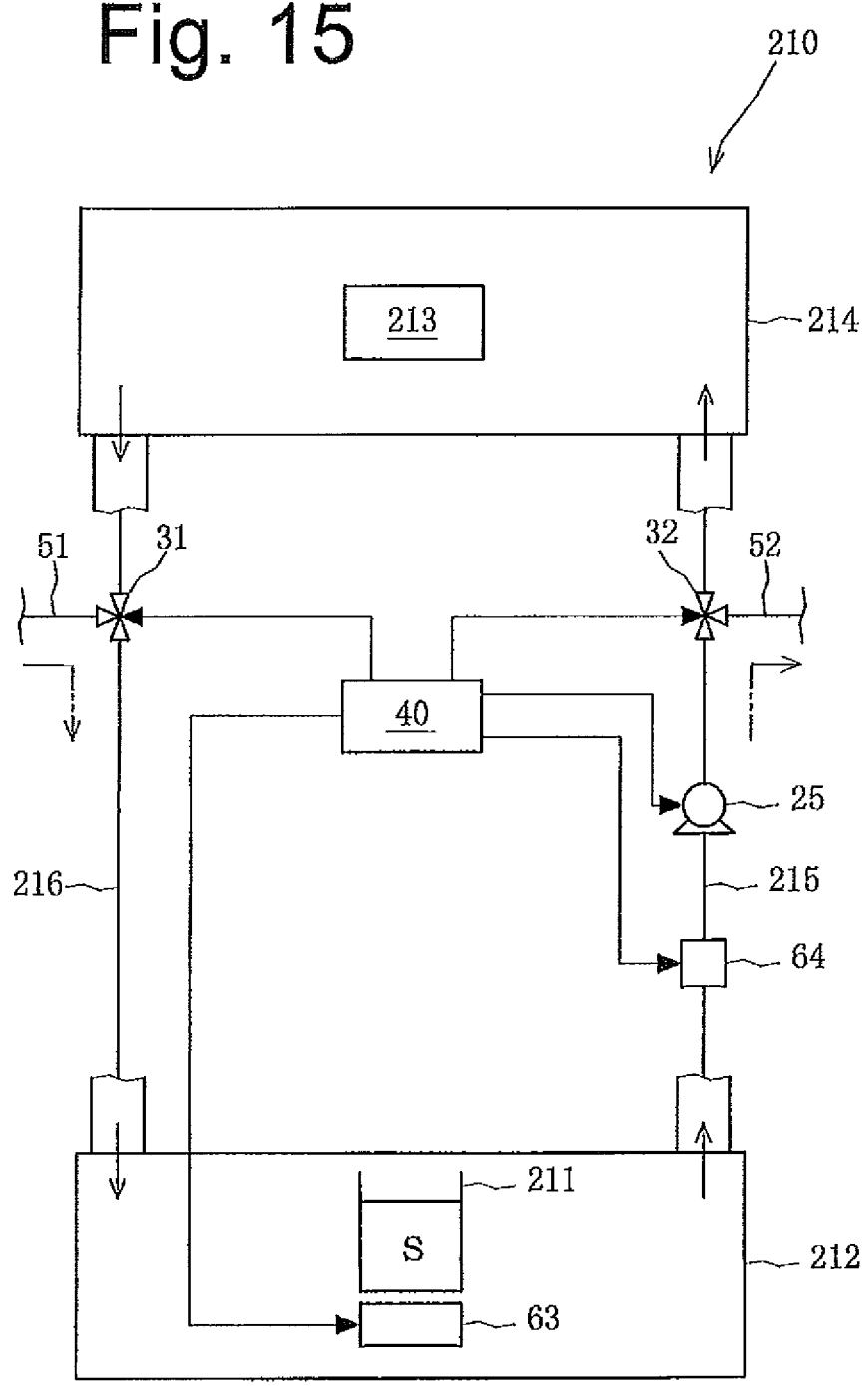
FIG. 15 is an explanatory diagram showing an outline of a third concentration measuring device.

As shown in FIG. 15, the concentration measuring device 210, for example, includes: a container 211 having a living thing S therein; an airtight case 212 for holding the container 211 therein; a concentration sensor 213; a concentration measuring case 214 for holding the concentration sensor 213 therein; a feed pipe 215 for sending a gas from the airtight case 212 to the concentration measuring case 214; a return pipe 216 for allowing the gas from the concentration measuring case 214 to be returned to the airtight case 212; the pump 25 provided in the feed pipe 215; the heater 63 for heating the container 211; and the control unit 40 for controlling these components. Furthermore, the concentration measuring device 210 may include the flow sensor 64, the first three-way valve 31 to be in communication with the outside via the intake pipe 51, and the second three-way valve 32 to be in communication with the outside via the exhaust pipe 52, if needed.

Examples of the living thing S may include animals such as microorganisms, fish, and insects and plants. Also, the concentration sensor 213 can detect a concentration of a predetermined gas (for example, carbon dioxide or oxygen).

According to the concentration measuring device 210, by measuring the concentration of the gas while appropriately changing an environmental condition (for example, temperature) in the container 211, it is also possible to examine a correlation between the environmental condition and an activity (breathing, photosynthesis, or the like) of the living thing. Furthermore, the concentration measuring device 210 has a circulation path formed by the concentration measuring case 214, the airtight case 212, the feed pipe 215, and the return pipe 216, the concentration of the predetermined gas generated from the living thing (sample) S can be measured easily and reliably without performing elaborate flow rate control by means of the pump 25. Furthermore, by continuously recording detection results from the concentration sensor 213, it becomes possible to know a history regarding the amounts of the predetermined gas generated from the sample S.

Figure 16:
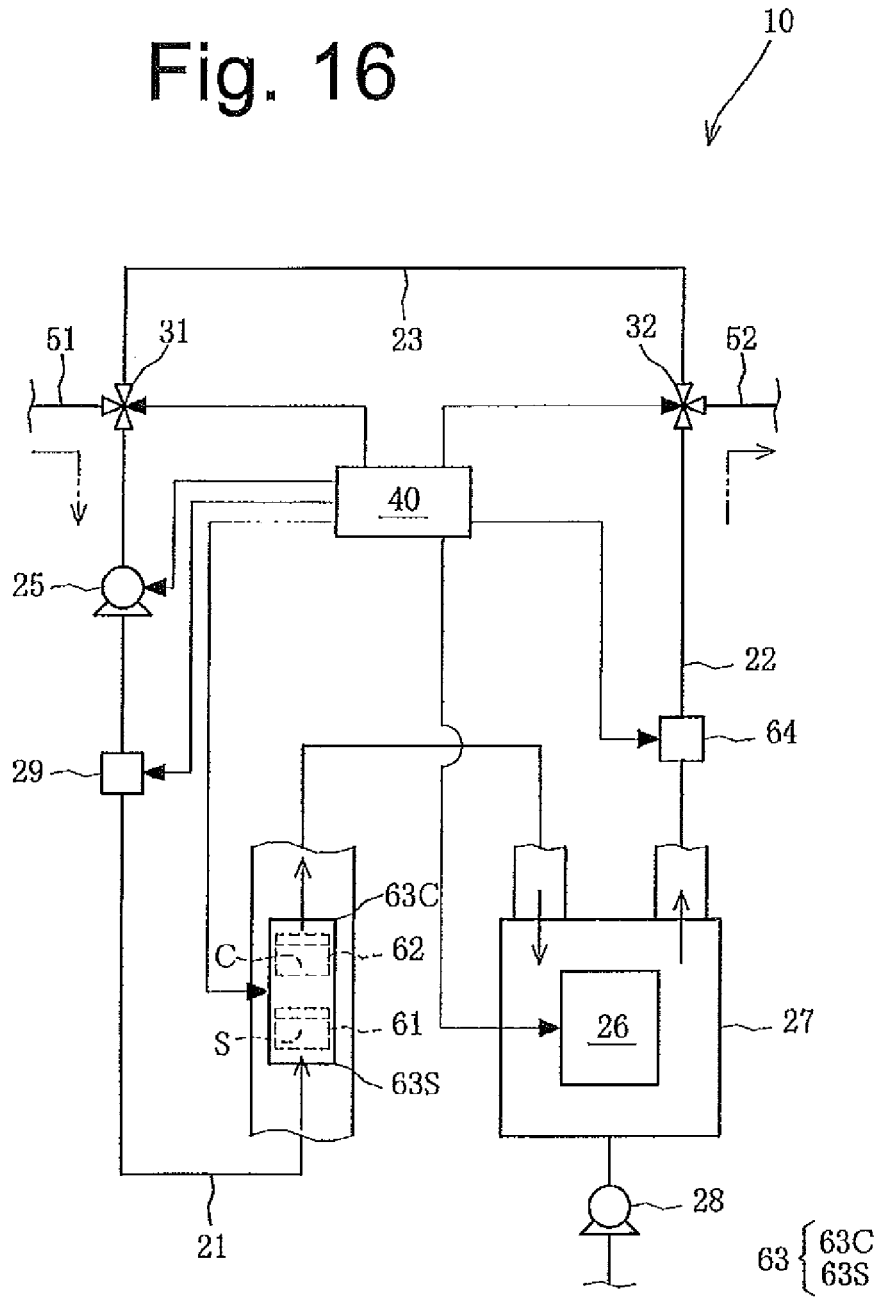
FIG. 16 is an explanatory diagram showing an outline of a fourth concentration measuring device.

As shown in FIG. 16, a concentration sensor 29 disposed upstream of the detection chamber 27 may be provided together with the concentration sensor 26 disposed downstream of the detection chamber 27. The measurement performance of the concentration sensor 29 is preferably equivalent to that of the concentration sensor 26.

The concentration sensor 29 is located closer to the external space, i.e., the intake pipe 51 and the first three-way valve 31, as compared to the concentration sensor 26. Thus, the concentration sensor 29 can measure the concentration of carbon dioxide in the outside air introduced from the intake pipe 51. On the other hand, while the concentration sensor 26 can measure the concentration of carbon dioxide in the introduced outside air, it cannot separate the concentration of carbon dioxide remaining in the circulation path from this measurement result. In other words, the concentration sensor 29 can measure the concentration of carbon dioxide in the outside air more accurately than the concentration sensor 26.

Furthermore, in a case where the concentration sensor 26 and the concentration sensor 29 are both used, the control unit 40 can also perform a concentration sensor malfunction determination process to be described next.

In the concentration sensor malfunction determination process, the control unit 40 simultaneously reads the detected value from the concentration sensor 26 and that from the concentration sensor 29, and calculates a difference between these detected values. Furthermore, the control unit 40 compares the difference between the detected values to a threshold value stored in a memory in advance. In a case where the comparison result indicates that the difference between the detected values is smaller than the threshold value, the control unit 40 determines that the concentration sensor 26 and the concentration sensor 29 are normally operated. In a case where the comparison result indicates that the difference between the detected values is greater than the threshold value, on the other hand, the control unit 40 can determine that either the concentration sensor 26 or the concentration sensor 29 is abnormally operated. This concentration sensor malfunction determination process is performed under a condition where the concentration of carbon dioxide in the pipe is at a constant level (for example, in the background measurement process 81).

Moreover, in a case where the concentration sensor 26 and the concentration sensor 29 are both used, the control unit 40 can also perform an exhaust completion determination process or a measurability determination process to be described next.

In the exhaust completion determination process, the control unit 40 compares a difference between detected values in the cooling process 84 to a threshold value stored in the memory in advance. In a case where the comparison result indicates that the difference between the detected values is smaller than the threshold value, the control unit 40 determines that the gas inside the pipe is replaced with the outside air. In a case where the comparison result indicates that the difference between the detected values is greater than the threshold value, on the other hand, the control unit 40 determines that the gas inside the pipe has not yet been replaced with the outside air. The exhaust completion determination process is performed when the outside air is introduced into the pipe (for example, in the cooling process 84 to be performed after all the main measurement processes 83 are completed).

In the measurability determination process, the control unit 40 compares a difference between detected values in the cooling process 84 to a threshold value stored in the memory in advance. In a case where the difference between the detected values is greater than the threshold value and the detected value from the concentration sensor 26 is smaller than that from the concentration sensor 29, the control unit 40 determines that carbon dioxide is adsorbed onto the catalyst C due to a temperature decrease in the catalyst C associated with the replacement operation of the sample S or the like, for example. In a case where the difference between the detected values is greater than the threshold value and the detected value from the concentration sensor 29 is smaller than that from the concentration sensor 26, on the other hand, the control unit 40 determines that the outside air has been introduced from the intake pipe 51, for example. In other words, in a case where the comparison result indicates that the difference between the detected values is greater than the threshold value, the control unit 40 determines that the main measurement process 83 cannot be performed following this cooling process 84. In a case where the difference between the detected values is smaller than the threshold value, on the other hand, the control unit 40 determines that the main measurement process 83 can be performed following this cooling process 84. The measurability determination process is performed in the cooling process 84 to be performed before the main measurement process 83.

The present invention is not limited to the embodiments described above. It is to be understood that various modifications can be made without departing from the scope of the invention.

The entire disclosure of Japanese Patent Application No. 2012-275611 filed on Dec. 18, 2012 and No. 2013-216317 filed on Oct. 17, 2013 including specification, claims, drawings, and summary are incorporated herein by reference in its entirety.

What is claimed is:

1. A concentration measuring device comprising:
   a circulation path forming member that forms a circulation path through which a gas can circulate in a closed state in which the circulation path is closed off from outside;
   a sample container for holding a sample provided in the circulation path;
   a circulation device for flowing the gas in a predetermined circulating direction in the circulation path; and
   a concentration measuring mechanism provided in the circulating path for measuring a concentration of a target substance from the sample contained in the gas circulating in the closed state of the circulation path.

2. The concentration measuring device according to claim 1, wherein the concentration measuring mechanism includes:
   a sample heater for heating the sample;
   a catalyst located in the circulation path downstream of the sample in the circulation direction;
   a catalyst heater for heating the catalyst;
   a test substance detecting part provided in the circulation path downstream of the catalyst in the circulating direction, for detecting a test substance generated by a reaction between the catalyst and the target substance;
   a concentration sensor for detecting a concentration of the test substance in the test substance detecting part; and
   an output part for outputting the concentration of the test substance detected by the concentration sensor to a calculation part that calculates a concentration of the target substance from the concentration of the test substance.

3. The concentration measuring device according to claim 2, wherein the circulation path includes a return path for allowing the gas exiting from the test substance detecting part to be returned to the sample.

4. The concentration measuring device according to claim 3, wherein the concentration sensor detects a concentration of the test substance for the gas having passed through the return path.

5. The concentration measuring device according to claim 2, further comprising a catalyst container for holding the catalyst therein, and
   wherein a relative position between the catalyst container or the catalyst heater and the sample container can be switched between a first state in which they are separated from each other and a second state in which they are closer to each other as compared to the first state.

6. The concentration measuring device according to claim 5, wherein the sample container is movable, and the catalyst container is fixed.

7. The concentration measuring device according to claim 5, further comprising a heater controlling part for controlling the sample heater and the catalyst heater, and
   wherein the heater controlling part controls the sample heater in such a manner that heating of the sample is performed in the second state and heating of the sample is stopped in the first state, and controls the catalyst heater in such a manner that heating of the catalyst is performed in each of the first state and the second state.

8. The concentration measuring device according to claim 2, further comprising a controlling part for controlling the sample heater and the catalyst heater, and
   wherein the controlling part controls to perform heating of the sample and the catalyst in a step of measuring a concentration of the target substance and controls to perform heating of the catalyst and stop heating of the sample before or after the step of measuring the concentration of the target substance.

9. The concentration measuring device according to claim 2, wherein the catalyst heater and the sample heater are integrally formed.

10. The concentration measuring device according to claim 2, further comprising a switching mechanism capable of switching the circulation path forming member between an air intake and exhaust state in which an outside air is introduced toward the sample and the gas exiting from the test substance detecting part is discharged to an outside and a circulation state in which the gas exiting from the test substance detecting part is returned to the sample.

11. The concentration measuring device according to claim 2, further comprising a cooling device for cooling the catalyst or the sample, and
   wherein the cooling device includes a switching mechanism capable of switching the circulation path forming member between an air intake and exhaust state in which an outside air is introduced toward the sample and the gas exiting from the test substance detecting part is discharged to an outside and a circulation state in which the gas exiting from the test substance detecting part is returned to the sample.

12. The concentration measuring device according to claim 10, wherein:
   the switching mechanism includes
      a first switching valve provided in the circulation path between the sample and the test substance detecting part,
      a second switching valve provided in the circulation path between the first switching valve and the test substance detecting part, and
      a switching valve controller for controlling the first and second switching valves;
   each of the first and second switching valves can preferably change a path between an open state in which the circulation path is opened to the outside and a closed state in which the circulation path is closed off from the outside; and
   the switching valve controller sets the first and second switching valves to the open state so that the circulation path forming member is set in the air intake and exhaust state and sets the first and second switching valves to the closed state so that the circulation path forming member is set in the circulation state.

13. The concentration measuring device according to claim 12, wherein
   when a process of causing the concentration sensor to detect a concentration of the test substance in the test substance detecting part while the first and second switching valves are both in the closed state and the sample heater and the catalyst heater are turned ON is defined as a main measurement process,
   the switching valve controller maintains the first and second switching valves in the closed state until passage of a predetermined amount of time after start of the main measurement process and changes both of the first and second switching valves to the open state once the predetermined amount of time has elapsed.

14. The concentration measuring device according to claim 1, further comprising a flow path volume changing mechanism capable of changing a volume of a flow path formed by the circulation path forming member.

15. The concentration measuring device according to claim 2, further comprising an upstream-side concentration sensor disposed upstream of the sample in the circulating direction, for detecting a concentration of the test substance.

\* \* \* \* \*